(12) United States Patent
Norton et al.

(10) Patent No.: US 8,877,225 B2
(45) Date of Patent: Nov. 4, 2014

(54) CONTROLLED RELEASE COPOLYMER FORMULATION WITH IMPROVED RELEASE KINETICS

(75) Inventors: Richard L. Norton, Ft. Collins, CO (US); Eric Dadey, Furlong, PA (US)

(73) Assignee: Tolmar Therapeutics, Inc., Fort Collins, CO (US)

( * ) Notice: Subject to any disclaimer, the term of this patent is extended or adjusted under 35 U.S.C. 154(b) by 0 days.

(21) Appl. No.: 12/477,805

(22) Filed: Jun. 3, 2009

(65) Prior Publication Data

US 2009/0325879 A1    Dec. 31, 2009

Related U.S. Application Data

(60) Provisional application No. 61/058,477, filed on Jun. 3, 2008.

(51) Int. Cl.
| | |
|---|---|
| *A61F 2/00* | (2006.01) |
| *A61K 47/30* | (2006.01) |
| *A61P 5/02* | (2006.01) |
| *A61P 23/00* | (2006.01) |
| *A61P 29/00* | (2006.01) |
| *A61K 38/31* | (2006.01) |
| *A61K 31/59* | (2006.01) |
| *A61K 9/00* | (2006.01) |
| *A61K 47/34* | (2006.01) |
| *A61K 38/09* | (2006.01) |
| *A61K 31/519* | (2006.01) |
| *A61K 47/22* | (2006.01) |
| *A61K 47/20* | (2006.01) |
| *A61K 47/10* | (2006.01) |
| *A61K 47/18* | (2006.01) |

(52) U.S. Cl.
CPC .............. *A61K 38/09* (2013.01); *A61K 47/22* (2013.01); *A61K 47/20* (2013.01); *A61K 9/0024* (2013.01); *A61K 47/34* (2013.01); *A61K 38/31* (2013.01); *A61K 47/10* (2013.01); *A61K 31/519* (2013.01); *A61K 47/18* (2013.01)
USPC .......... 424/426; 424/423; 424/424; 514/10.3; 514/10.4; 514/12.2; 514/18.3; 514/772.3; 514/259.1; 530/311

(58) Field of Classification Search
None
See application file for complete search history.

(56) References Cited

U.S. PATENT DOCUMENTS

| | | | |
|---|---|---|---|
| 5,278,201 A | 1/1994 | Dunn et al. | |
| 5,278,202 A | 1/1994 | Dunn et al. | |
| 5,324,519 A | 6/1994 | Dunn et al. | |
| 5,340,849 A | 8/1994 | Dunn et al. | |
| 5,487,897 A | 1/1996 | Polson et al. | |
| 5,599,552 A | 2/1997 | Dunn et al. | |
| 5,681,873 A | 10/1997 | Norton et al. | |
| 5,702,716 A | 12/1997 | Dunn et al. | |
| 5,733,950 A | 3/1998 | Dunn et al. | |
| 5,736,152 A | 4/1998 | Dunn | |
| 5,739,176 A | 4/1998 | Dunn et al. | |
| 5,744,153 A | 4/1998 | Yewey et al. | |
| 5,759,563 A | 6/1998 | Yewey et al. | |
| 5,780,044 A | 7/1998 | Yewey et al. | |
| 5,792,469 A | 8/1998 | Tipton et al. | |
| 5,945,115 A | 8/1999 | Dunn et al. | |
| 5,990,194 A | 11/1999 | Dunn et al. | |
| 6,143,314 A | 11/2000 | Chandrashekar et al. | |
| 6,261,583 B1 | 7/2001 | Dunn et al. | |
| 6,355,657 B1 | 3/2002 | Osborne | |
| 6,395,293 B2 | 5/2002 | Polson et al. | |
| 6,461,631 B1 | 10/2002 | Dunn et al. | |
| RE37,950 E | 12/2002 | Dunn et al. | |
| 6,528,080 B2 | 3/2003 | Dunn et al. | |
| 6,565,874 B1 | 5/2003 | Dunn et al. | |
| 7,019,106 B2 | 3/2006 | Yamamoto et al. | |
| 2005/0244469 A1* | 11/2005 | Whitcup et al. | .............. 424/427 |
| 2008/0194663 A1 | 8/2008 | Dunn | |

FOREIGN PATENT DOCUMENTS

| | | |
|---|---|---|
| WO | WO-02/38185 A2 | 5/2002 |
| WO | WO-02/49573 A2 | 6/2002 |
| WO | WO-2006/065951 A2 | 6/2006 |
| WO | WO-2008/045516 A1 | 4/2008 |
| WO | WO-2008/100532 A1 | 8/2008 |
| WO | WO-2009/148580 A2 | 12/2009 |

OTHER PUBLICATIONS

"International Application Serial No. PCT/US2009/003362, International Search Report mailed Oct. 12, 2010", 4 pgs.
"International Application Serial No. PCT/US2009/003362, Written Opinion mailed Oct. 12, 2010", 10 pgs.
Dadey, E., et al., "Low Burst Polymers and Methods to Produce Polymer", U.S. Appl. No. 60/901,435, filed Feb. 15, 2007, 39 pgs.
"European Application Serial No. 09758744.8, Office Action mailed Feb. 24, 2011", 3 pgs.
"European Application Serial No. 09758744.8, Response filed Apr. 6, 2011 to Office Action mailed Feb. 24, 2011", 19 pgs.
"Australian Application Serial No. 2009255675, First Examiner Report mailed Sep. 4, 2013", 4 pgs.
"Chinese Application Serial No. 200980130106,0, Office Action mailed Jul. 22, 2013", (w/ English Translation), 6 pgs.

(Continued)

*Primary Examiner* — Jeffrey T Palenik
(74) *Attorney, Agent, or Firm* — Schwegman Lundberg & Woessner, P.A.

(57) ABSTRACT

The present invention provides a constant release copolymer composition adapted for use in a controlled release formulation for a bioactive agent, such as a formulation adapted for implantation within a patient's body tissues as a depot to release the agent over a period of time, wherein the copolymer provides a substantially constant rate of release of the bioactive agent over the time period for which the depot persists in the body tissues. The copolymer includes a PLG copolymer and a PLG oligomer of about 5-10 kDa average molecular weight, which can lack free carboxylic acid groups. When the PLG copolymer is a low burst copolymer, the constant release copolymer composition is a low burst, constant release copolymer composition adapted for implantation in the body tissues of a mammal, wherein a substantially constant rate of release of the bioactive agent is achieved.

33 Claims, 8 Drawing Sheets

(56) References Cited

OTHER PUBLICATIONS

"Chinese Application Serial No. 200980130106.0, Office Action mailed Nov. 8 2013", (w/English Translation), 6 pgs.

"Chinese Application Serial No. 200980130106.0, Response filed Oct. 8, 2013 to Office Action mailed Jul. 22, 2013", (w/ English Translation of Claims), 12 pgs.

"European Application Serial No. 09758744.8, Office Action mailed Nov. 12, 2013", 5 pgs.

"Australian Application Serial No. 2009255675, Response filed Jan. 13, 2014 to First Examiner Report mailed Sep. 4, 2013", 17 pgs.

"Chinese Application Serial No. 200980130106.0, Response filed Jan. 15, 2014 to Office Action mailed Nov. 8, 2013", (w/ English Translation of Amended Claims), 18 pgs.

"Chinese Application Serial No. 200980130106.0, Office Action mailed May 3, 2012", (w/ English Translation), 11 pgs.

"Chinese Application Serial No. 200980130106.0, Office Action mailed Apr. 1, 2013", (w/ English Translation), 13 pgs.

"Chinese Application Serial No. 200980130106.0, Response filed Jun. 17, 2013 to Office Action mailed Apr. 1, 2013", (w/ English Translation of Amendment Claims), 11 pgs.

"Chinese Application Serial No. 200980130106.0, Response filed Nov. 19, 2012 to Office Action mailed May 3, 2012", (w/ English Translation), 18 pgs.

"Australian Application Serial No. 2009255675, Second Examiner Report mailed Feb. 5, 2014", 4 pgs.

\* cited by examiner

CONTROLLED RELEASE COPOLYMER FORMULATION WITH IMPROVED RELEASE KINETICS

CLAIM OF PRIORITY

Benefit of priority is hereby claimed to U.S. Provisional Patent Application Ser. No. 61/058,477, filed on Jun. 3, 2008 and entitled Controlled Release Copolymer Formulation with Improved Release Kinetics, the specification of which is herein incorporated by reference in its entirety.

BACKGROUND

Copolymer compositions adapted for use in controlled release delivery systems such as biodegradable and bioerodible implants are known. Polyesters such as poly(DL-lactide-glycolide) ("PLG") copolymers can be used, as the ester linkages are readily degraded in body tissues by endogenous esterases as well as by uncatalyzed hydrolytic cleavage yielding non-toxic, water-soluble hydrolysis products, and controlled release systems incorporating PLG copolymers have been widely described. See, for example, U.S. Pat. Nos. 7,019,106; 6,565,874; 6,528,080; RE37,950; 6,461,631; 6,395,293; 6,355,657; 6,261,583; 6,143,314; 5,990,194; 5,945,115; 5,792,469; 5,780,044; 5,759,563; 5,744,153; 5,739,176; 5,736,152; 5,733,950; 5,702,716; 5,681,873; 5,599,552; 5,487,897; 5,340,849; 5,324,519; 5,278,202; and 5,278,201. Such controlled release systems are in general advantageous because they provide for the controlled and sustained release of medications, often directly at or near the desired site of action, over the period of days, weeks or even months. Polyesters including poly-lactide, poly-glycolide, and copolymers thereof ("PLG copolymers") can be prepared from glycolide (1,4-dioxan-2,5-dione, glycolic acid cyclic dimer lactone) and lactide (3,6-dimethyl-1,4-dioxan-2,5-dione, lactic acid cyclic dimer lactone), or from glycolate (2-hydroxyacetate) and lactate (2-hydroxypropionate). These copolymer materials are particularly favored for this application due to their facile breakdown in vivo by body fluids or enzymes in the body to non-toxic materials, and their favorable properties in temporally controlling the release of medicaments and biologically active agents ("bioactive agents") that may be contained within a mass of the controlled release formulation incorporating the polymer that has been implanted within a patient's body tissues. Typically, controlled release systems are adapted to provide for as constant a rate of release as possible of the bioactive agent over the time period that the implant persists within the body.

Flowable delivery systems, such as the Atrigel® systems, are disclosed in U.S. Pat. Nos. 6,565,874, 6,528,080, 6,461, 631, 6,395,293, and references found therein. Flowable delivery systems like the Atrigel® system include a biodegradable polymer such as a PLG copolymer, a bioactive agent, and an organic solvent that has at least a very slight solubility in body fluids. When the substantially liquid ("flowable") solution of the delivery system is injected into a patient's tissues, typically as a single bolus, the organic solvent diffuses into surrounding body fluids, causing precipitation or gelation of the water-insoluble polymer containing the bioactive agent. It is believed that initially a skin forms on the deposited liquid mass, bringing about formation of the semi-solid deposit known as a depot that contains the remaining solution of the polymer and the bioactive agent in the solvent. As the depot resides in the tissues, the solvent continues to diffuse out and body fluids to diffuse in, bringing about ongoing precipitation of the polymer with the bioactive agent, until a gelled or solid mass remains. Channels or pores may form in the depot as part of this process. Due to the biodegradable nature of the polymer in the presence of body fluids and of enzymes within the body, the polymer slowly degrades into soluble non-toxic hydrolysis products, releasing the contained bioactive agent over a period of time. This process continues until the depot is substantially completely dissolved and all the bioactive agent is released. It is understood that such depots can be adapted to persist for various lengths of time within the body, such as about 30 days, about 60 days, or about 3 months, 4 months, or 6 months.

In this manner, a relatively constant level of the bioactive agent can be maintained within the patient's body for the period of time over which the formulation is adapted to release the agent. It is generally undesirable to have fluctuations in the rate of release, and thus in the levels within the patient's body, of the bioactive agent following as well as during the initial period following administration of the formulation to the patient. For example, it is undesirable to have an increasing rate of release or a decreasing rate of release, or to have the rate of release peak at some time point and then decline, during the entire time period for which the formulation is adapted to release the bioactive agent. The most desirable rate of release is typically a constant, or zero-order, rate of release, wherein the amount of the bioactive agent released per time interval is constant, up until the point of complete dissolution of the controlled release implant in the patient's body.

At least two problems involving a less than optimal rate of release have been found using art PLG copolymers in controlled release systems: an initial burst effect, and a degree of variability in the subsequent rate of release over the lifetime of the depot in the body. It has been found that the release of many bioactive agents such as peptides, proteins, and small molecule drugs from controlled release systems can occur at a higher than optimal rate during the first 24 hours after implantation under certain conditions. This is known in the art as the "burst effect" or the "initial burst effect," and is generally undesirable, as overdosing of the patient can result. A number of approaches to the solution of the burst effect problem have been described, as are discussed below. The second effect involves a variable, non-linear rate of release of the bioactive agent as the implanted formulation undergoes its period of degradation in the body that deviates from linearity or zero-order kinetics. This effect can occur when using purified copolymer formulations adapted to reduce or minimize the initial burst effect as well as when using unpurified copolymers. After a depot has been formed within a patient's body by introduction of a flowable delivery system, it has been observed on occasion that the rate of release of the bioactive agent tends to vary. Thus, while the depot is present within the body an increase or a decrease or a variation in rate of delivery of the bioactive agent occurs, which is generally undesirable.

SUMMARY OF THE INVENTION

Various embodiments of the present invention, constant release copolymer formulations as defined herein, when used in a flowable delivery system such as an Atrigel® system, provide for substantially more constant rates of release of bioactive agents over the period of time that the depot persists within the body tissues of a patient. This relatively constant rate of release results in an improved release profile compared to other copolymer formulations, because it tends to maintain a more constant level of the bioactive agent with the body tissues, which is generally desirable from a medical perspective. For example, controlled release formulations involving various embodiments of the inventive constant release copolymer have unexpectedly been found to reduce variations in the rate of release of the bioactive agent, especially later in the process of dissolution of the implanted depot, resulting in a release profile closer to a "zero-order", i.e., linear, rate of release.

Various embodiments of the constant release copolymer formulations of the present invention, including of a mixture of a PLG copolymer and a PLG oligomer (referred to hereinafter as a "constant release copolymer composition"), when incorporated into a controlled release formulation for a bioactive agent, provides for a substantially constant rate of release of the bioactive agent from a depot over substantially the entire period of time that the depot persists in the patient's body tissues. The PLG copolymer used in the inventive constant release copolymer composition can be one of the well-known PLG copolymers as described in U.S. Pat. Nos. 6,565,874, 6,528,080, 6,461,631, 6,395,293, and elsewhere.

Alternatively, the PLG copolymer can be a purified PLG copolymer that can be of the type that when incorporated into a controlled release formulation of the Atrigel® type provides for a reduced initial burst effect (referred to hereinafter as a "low burst copolymer"). When an inventive constant release copolymer mixture includes a low burst PLG copolymer and a PLG oligomer as defined herein, a "low burst, constant release copolymer composition" is obtained. The low burst PLG copolymer can be a solvent precipitation-purified PLG copolymer such as is described in patent application U.S. Ser. No. 60/901,435, filed Feb. 15, 2007, by the inventors herein, which can be referred to as a PLG(p) copolymer. Or, the low burst PLG copolymer can be a copolymer incorporating a "core diol" unit, such as the copolymer obtained when hexane-1,6-diol is used as an initiator for polymerization of lactide and glycolide, producing a PLG copolymer with substantially no free carboxylic acid end groups, as is described in patent application U.S. Ser. No. 11/469,392, filed Aug. 31, 2006, by the inventors herein. Alternatively, the low burst PLG copolymer can be can be a PLG copolymer purified by a supercritical fluid extraction (SFE) process, as described in PCT/US2007/021749, filed Oct. 11, 2007, by the inventors herein, wherein the SFE-purified PLG copolymer can have a relatively narrow distribution of individual polymer molecular weights, a limited content of monomers, undesirable short-chain PLG copolymers, and copolymer molecules with excessively high individual molecular weights.

When the PLG copolymer and the PLG oligomer are combined, a constant release copolymer composition is obtained that unexpectedly provides for a greater linearity of release of a bioactive substance over time after implantation in body tissues when the constant release copolymer composition, the bioactive substance, and an organic solvent that is at least somewhat soluble in body fluids are combined in an Atrigelφ type controlled release formulation and implanted into the living tissue of a mammal.

The PLG oligomer can be an oligomer comprising lactide or glycolide units, or both, wherein the average molecular weight of the oligomer is less than about 10 kDa, preferably about 7-8 kDa. For example, the PLG oligomer can be a pure poly(lactide), termed a "PLA", wherein the lactide content is 100%. Alternatively, the PLG oligomer can be a "65/35-PLG", wherein the lactide content is 65% and the glycolide content is 35%. The PLG oligomer can be substantially free of terminal carboxylic acid groups, for example having any such carboxylic acids capped as esters such as methyl esters. The PLG oligomer can also be substantially free of any carboxylic acid groups distributed on the molecular chain.

Various embodiments of the inventive constant release copolymer composition, when incorporated into a flowable delivery formulation, reduces or minimizes variations in the rate of release of the bioactive agent over the period of time that the depot persists within the patient's body tissue, compared to a flowable delivery system containing an art copolymer. This control persists until biodegradation of the depot is complete. In particular, use of the inventive constant release copolymer composition avoids a decrease or an increase in the rate of release of the agent as the depot nears the end of its time of residence in the body, that is, immediately prior to final dissolution of the depot.

Another advantage is realized when an embodiment of a low burst, constant release copolymer composition of the invention is incorporated into a controlled release formulation of the Atrigel® type. Here, the initial burst effect is minimized and the rate of release of the bioactive agent over the lifetime of the depot within the patient's body is kept at a more constant level than is observed with art delivery systems, thus overcoming two of the major disadvantages of controlled delivery systems presently in use.

An embodiment of the present invention provides a constant release copolymer composition that includes a mixture of a PLG copolymer and a PLG oligomer of less than about 10 kDa. The oligomer can be substantially lacking in carboxylic end groups. The inventive constant release copolymer composition is adapted for use in a controlled release formulation for release of a bioactive agent from a depot within a patient's body tissues, the formulation providing a substantially constant rate of release of the agent over a period of time that the depot persists within the body tissues. The relatively constant rate of release of the bioactive substance by the depot results in a relatively constant level of the bioactive substance in the patient's body, which is generally desirable from a medical perspective.

Various embodiments of the present invention further provide methods of preparing the inventive formulation, involving combining a PLG oligomer and a PLG copolymer, a bioactive agent, and an organic solvent having at least a very slight solubility in body fluids.

Various embodiments of the present invention further provide methods of administering a bioactive agent to a patient over a prolonged period of time, wherein a substantially constant rate of release of the bioactive agent is achieved, comprising administering to the patient a controlled release formulation comprising the inventive copolymer formulation, the bioactive agent, and an organic solvent having at least a very slight solubility in body fluids.

Various embodiments of the present invention further provide the use of the controlled release formulation described herein in the manufacture of a medicament for administering a bioactive agent to a patient over a prolonged period of time, wherein a substantially constant rate of release of the bioactive agent is achieved. In some embodiments, the formulation is administered as a depot. In some embodiments, the depot is emplaced subcutaneously. In certain embodiments, the patient suffers from a malcondition and the bioactive agent is adapted to treat, arrest, or palliate the malcondition. In preferred embodiments, the malcondition is prostate cancer and the agent is leuprolide. In other preferred embodiments, the malcondition is acromegaly and the agent is octreotide. In still other preferred embodiments, the malcondition is psychosis and the agent is risperidone. In still other preferred embodiments, the malcondition is pain and the agent is an analgesic or an anti-inflammatory.

BRIEF DESCRIPTION OF THE DRAWINGS

In all the figures, averages are plotted with error bars of one standard error.

DETAILED DESCRIPTION OF THE INVENTION

Definitions

Figure 1:
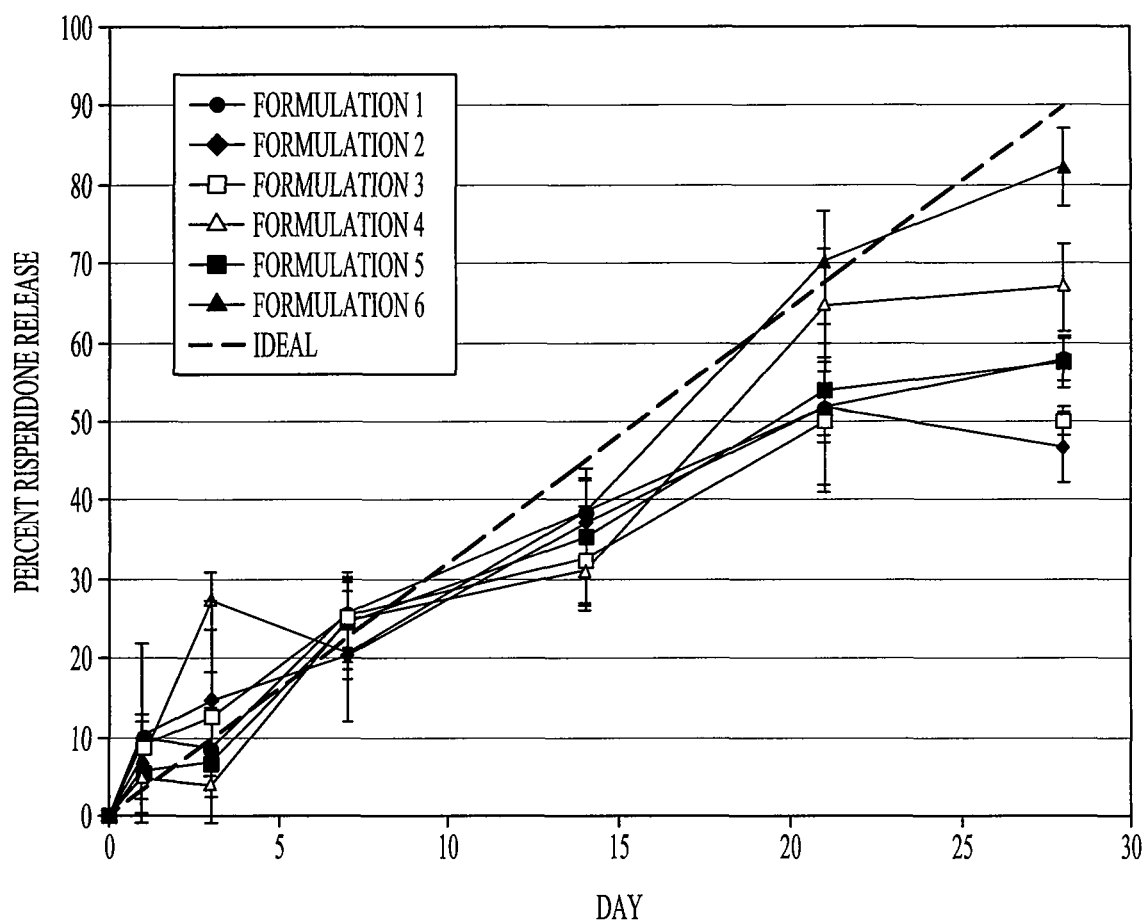
In FIG. 1 the release profiles of risperidone from depots formed using a flowable delivery system in rats are shown. The system is adapted to release risperidone over a period of about 28 days, and a zero-order, constant release rate would exhibit the ideal straight line as shown, with about 90% of the agent being released over the 28 day period. The control formulation, including 15% risperidone in copolymer PLGH (p) (a purified 80/20 PLGH, i.e., 80 mole % lactide, 20 mole % glycolide, and free carboxylic acid end groups) without any added PLG oligomer, in N-methylpyrrolidone (NMP) solution, release profile is indicated by closed circles. The closed diamonds indicates the release from an equivalent formulation but with unpurified 80/20 PLGH. The other symbols indicate the release from inventive constant release copolymer formulations.

A "copolymer" or a "PLG copolymer" as the terms are used herein refer to a poly(lactide-glycolide) polymer formed of lactide (or lactate) and glycolide (or glycolate) units in a defined molar proportion. The molar proportion can range from 100 mole % lactide to 100 mole % glycolide but typically ranges from about 50-100 mole % lactide. Thus, a pure poly(lactide), i.e., 100 mole % lactide, also known as PLA, is a PLG copolymer within the meaning herein. Copolymers composed of both lactide and glycolide units can be described in terms of their molar compositions; i.e., a 65/35 PLG is understood to consist of 65 mole % lactide units and 35 mole % glycolide units. A copolymer can include neutral poly(lactide-glycolide) molecular chains that terminate in alcohol or ester groups, or ionic poly(lactide-glycolide) molecular chains that terminate in carboxylic acid groups (also referred to as PLGH copolymers). PLG copolymers, as the term is used herein, include compositions referred to in the art as poly(lactate-glycolate), poly(lactate(co)glycolate), poly(lactide-glycolide), poly(lactide(co)glycolide), and the like, with the understanding that additional moieties may be included, such as core or initiator groups (for example, diols, hydroxyacids, and the like), capping groups (for example, esters of terminal carboxyl groups, and the like) and other pendant groups or chain extension groups covalently linked to or within the polyester backbone, including groups that crosslink the substantially linear polyester molecular chains.

A "formulation" as the term is used herein is a composition including the inventive constant release copolymer composition plus a bioactive agent in a form adapted for administration to a patient for controlled release of the bioactive agent into the patient's body tissues.

Methods of preparation of these various types of PLG copolymer are well known in the art; for example a neutral PLG can be synthesized by catalyzed polymerization of lactide and glycolide reagents (cyclic dimers) from a core diol, such as hexane-1,6-diol, wherein ester bonds are formed between the end of the growing chains and the newly added lactide/glycolide units resulting in polymer chains wherein both ends have terminal hydroxyl groups, which are neutral, as is described in patent application U.S. Ser. No. 11/469,392 by the inventors herein. Alternatively, an ionic or acidic PLG (a PLGH) can be prepared by polymerization of lactide/glycolide reagents initiated by lactic acid, wherein one end of the PLG chain that is formed bears an ionizable carboxylic acid group. An acidic PLGH can be capped with an alcohol, that is, an ester group can be formed from the free carboxylic end group and the alcohol, to provide a neutral PLG copolymer within the meaning herein.

The terms "burst effect" or "initial burst effect" are used herein to refer to the situation in which a higher than average rate of diffusion of a bioactive agent out of a controlled release formulation occurs immediately following emplacement of a liquid delivery system, for example, within 1-2 days following emplacement. By "higher than average" is meant that during this initial time period following emplacement of the controlled release formulation with body tissues, the rate of release of the agent is higher than is seen on the average over the entire period of time that the implant continues to release the agent within the body tissues. Thus a burst effect represents a surge of the bioactive agent, which can amount to 25-30% of the total agent contained in the depot, immediately after emplacement that tapers off to the lower rate of release that occurs throughout the total time period that the depot persists within the body tissues. A "low burst copolymer" is a copolymer that, when incorporated into a controlled release formulation, for example of the Atrigel® type, provides for a low initial burst effect and avoids the undesired effects on the patient of a transient high level of the bioactive agent immediately following emplacement of the depot.

An "oligomer" or a "PLG oligomer" as the terms are used herein refers to a PLG copolymer as the term is defined above wherein the average molecular weight is about 5-10 kDa, preferably about 7-8 kDa. A "hydrophobic" PLG oligomer is an oligomer wherein the mole % of lactide units is greater than about 50%, i.e., the oligomer includes more lactide units than glycolide units. The proportion of lactide units can be equal to or greater than 65 mole %, up to and including 100 mole %. Lactide units, incorporating a side chain methyl group, are known to be more hydrophobic than are glycolide units, which lack the methyl group. A PLG oligomer that substantially lacks "free carboxylic acid groups" is a neutral PLG copolymer within the meaning herein, including only non-ionizable end groups such as hydroxyl groups or ester groups ("capped") and also lacking any pendant free carboxylic acid groups.

A "substantially constant rate of release" as used herein means that the release per unit time ("rate of release") of the bioactive agent from a depot of a controlled release formulation into the body of a patient is relatively constant over the period of time during which the formulation is adapted to release the agent. Thus, if the formulation is a "30-day" formulation, i.e., is adapted to release the agent over a period of time of about 30 days before the depot is completely biodegraded, a "substantially constant" rate of release means that every unit of time during that period, such as every day during that period, the amount of bioactive agent released into the patient's body is approximately a constant amount. This is also known in the art as "zero order release", i.e., if plotting the instantaneous rate of release of the bioactive agent vs. time, an equation of the type $y=kx^0$ describes the curve. If cumulative release versus time is plotted, a straight line having a slope corresponding to a linear cumulative release rate is seen. The later times in the period correspond to times when the depot is nearing complete dissolution in the body tissues. Once the depot is completely dissolved or biodegraded, release is likewise complete.

A "liquid delivery system" or a "flowable delivery system" is a combination of polymer, bioactive agent and organic solvent, such as in the Atrigel® system. After injection of the flowable material containing the polymer, agent, and solvent, into tissue as a single bolus, the solvent, which is at least slightly soluble in body fluids, disperses into the tissue and body fluid diffuses into the injected bolus, thereby causing coagulation of the polymer into a solid or semi-solid mass, which then undergoes biodegradation over time, releasing the bioactive agent. The organic solvent has at least a very slight solubility in body fluids, and can be completely soluble in body fluids, such that it can diffuse into the body fluids and vice versa. Solvents that can be used with the inventive polymers for a liquid or flowable delivery system include N-methylpyrrolidone, N,N-dimethylformamide, N,N-dimethylacetamide, dimethylsulfoxide, polyethylene glycol 200, polyethylene glycol 300, or methoxypolyethyleneglycol 350.

When the "molecular weight" or the "average molecular weight" of a copolymer or an oligomer is referred to, it is a weight average molecular weight, as is well known in the art. If the average molecular weight being referred to is the number-average molecular weight, it will be explicitly stated in this specification. When the individual molecular weights of the component individual molecules (molecular chains) are referred to, the term "individual molecular weight" is used herein or it will be clear that the molecular weight of a single polymer molecule is being referred to. Weight average molecular weights are determined by the use of gel permeation chromatography (GPC) with reference to polystyrene standards, as is well known in the art.

The term "polydispersity index" as used herein is defined as the weight-average molecular weight of a sample of a polymer material divided by the number-average molecular weight of the sample of the polymer material. The polydispersity index is well-known to relate to the distribution of molecular weights in a polymer. The higher the value of the polydispersity index, the broader the spread of individual molecular weights of the polymer molecular chains making up the polymer material. The lower the value of the polydispersity index, the more uniform and tightly grouped are the individual molecular weights of the individual polymer molecules making up the polymer material in question. In the unlikely event that every polymer molecule in the polymer material were identical, the weight-average molecular weight and the number-average molecular weight would be identical, and thus the polydispersity index ("PDI") would be unity in that case.

The terms "lactate" and "glycolate" as used herein, depending upon context, refer to either the hydroxyacids, lactic acid and glycolic acid respectively or their salts (lactates and glycolates) which can be used as reagents in preparation of PLG copolymers, or refer to those moieties as residues incorporated via ester bonds into the PLG copolymer polyester molecular chains. When a copolymer is formed by polymerization of lactic acid (lactate) and glycolic acid (glycolate), each molecular chain consists of individual lactate and glycolate monomeric units incorporated into the copolymer molecular chain by ester bonds.

The terms "lactide" and "glycolide" as used herein, depending upon context, refer to either the cyclic dimeric esters of lactate and glycolate respectively when referring to reagents used in preparation of PLG copolymers, or refer to those segments as incorporated ring-opened dimers in the formed PLG copolymer molecular chains. Thus, a statement about polymerization of lactide and glycolide refers to a polymerization reaction of the cyclic dimeric esters, whereas a statement about a lactide or glycolide residue within a copolymer molecular chain refers to that grouping of atoms, ring-opened, and incorporated into the copolymer chain. When a copolymer is formed by polymerization of lactide and glycolide, each incorporated lactide or glycolide residue includes a pair of lactate or glycolate monomeric units, respectively. It is understood that when a lactide and glycolide residue in a copolymer molecular chain is referred to, the terms mean double (dimeric) units of two lactate (L-L), or two glycolate (G-G), residues in the molecular chain, respectively, such as is believed to result from the polymerization of lactide and glycolide. When a lactate (L) or a glycolate (G) residue in a copolymer molecular chain is referred to, the terms mean single lactate (L) or glycolate (G) residues in the molecular chain, respectively, which can be within a lactide (L-L) or a glycolide (G-G) residue if the given lactate or glycolate is adjacent to another lactate or glycolate residue, respectively, regardless of the method used to prepare the copolymer molecular chain. As in most polymeric systems, this arrangement of residues is not all or none. Instead, the arrangement is a predominance. Thus, for the lactide and glycolide copolymers, a predominance of L-L and G-G residues will be present with some L and G (single) residues also present. The chemical reason underlying this characterization is the polymerization process. During polymerization, growing polymer chains are broken and reformed. This scission may split dimer residues and recombine single residues. For the lactate and glycolate copolymers, L and G (single) residues will be present on a statistical basis. This kind of polymer will have a relatively few sequences including repeats of dimer residues because of entropy factors.

It is understood that when the terms "lactic acid," "lactate," or "lactide" are used herein, that any and all chiral forms of the compounds are included within the terms. Thus, "lactic acid" includes D-lactic acid, L-lactic acid, DL-lactic acid, or any combination thereof; "lactide" includes DD-lactide, DL-lactide, LD-lactide, LL-lactide, or any combination thereof.

A substantially linear molecular chain that is formed by a polymerization process, such as a copolymer molecule that is within a copolymer material of the invention, has two ends, each end with a nearby "end domain," and an "internal domain" between the end domains. The terms are not exact, but rather describe general regions of a copolymer molecular chain, each end domain being the approximately 10-20% of the total length of the chain terminating at each of the two chain ends, and the internal domain being the remaining approximately 60-80% of the chain that lies between the end domains.

A "solvent" is an organic liquid that serves to dissolve a copolymer material to provide a homogeneous solution. The term "non-solvent" refers to a precipitation solvent, a usually organic liquid, that is not a solvent for the copolymer. It is in this context that the term "non-solvent" is used herein. Two liquids, such as a solvent and a non-solvent, are "miscible" when they combine with each other in all proportions without phase separation. Solvents may be "soluble" in each other but not "miscible" when they can combine without phase separation in some, but not in all, relative proportions. A solvent is "at least very slightly soluble in body fluids" when a measurable or significant quantity of the solvent is found to dissolve in aqueous liquid compositions with the properties of human body fluids. Typically the organic solvent is of sufficient solubility in body fluids to diffuse from an injected bolus into body fluids such that the contained copolymers can precipitate and form a skin surrounding the bolus to provide the solid or semi-solid depot.

DETAILED DESCRIPTION

The present invention is directed to a controlled release copolymer formulation including a constant release copolymer composition, which includes a mixture of a PLG copolymer and PLG oligomer, methods of making the copolymer composition, and methods of using the copolymer composition. Embodiments of the inventive constant release copolymer composition are adapted for use in controlled release formulations for release of a bioactive agent from a depot within a patient's body tissues, the formulation providing a substantially constant rate of release of the agent over a period of time that the depot persists within the body tissues.

As discussed above, controlled release formulations such as Atrigel® type flowable compositions, incorporating PLG copolymers, and also including purified PLG low-burst copolymers such as PLG(p) copolymers, can exhibit less than optimal non-linear kinetics of release of the bioactive agent after the initial burst period, especially late in the depot's lifetime. It has surprisingly been found that addition of a defined amount of a PLG oligomer to the PLG copolymer, the composition then being incorporated into a flowable delivery system that is emplaced within body tissues to form a depot, can result in improved linearity of release of the bioactive agent. As a result, the release profile of the agent over time more closely approximates a zero-order kinetics model. The PLG oligomer can be a relatively hydrophobic oligomer, with the lactate content ranging from about 60% to about 100%. The PLG oligomer can be substantially lacking free carboxylic acid groups, either terminal or pendant. It is additionally surprising that this addition of oligomer, particularly substitution of oligomer for a portion of base polymer, can be done without increasing the burst effect.

One type of low burst PLG copolymer, referred to herein as a "PLG(p) copolymer," is a PLG copolymer adapted for use in a controlled release formulation characterized by a weight average molecular weight of about 10 kilodaltons to about 50 kilodaltons and a polydispersity index of about 1.4-2.0, and having separated therefrom a copolymer fraction characterized by a weight average molecular weight of about 4 kDa to about 10 kDa and a polydispersity index of about 1.4 to 2.5. As is disclosed in U.S. Ser. No. 60/901,435 by the inventors herein, this PLG low-burst copolymer material can be prepared by dissolving a starting PLG copolymer material, which is not a product of hydrolysis of a higher molecular weight PLG copolymer material, in a solvent, then precipitating the low-burst copolymer material with a non-solvent. A PLG(p) copolymer can be a component of a constant release copolymer as disclosed and claimed herein.

Another type of low burst PLG copolymer, referred to herein as a "core diol" copolymer, as disclosed in patent application U.S. Ser. No. 11/469,392, is a PLG copolymer adapted for use in a controlled release formulation characterized by, for example, a structure as shown:

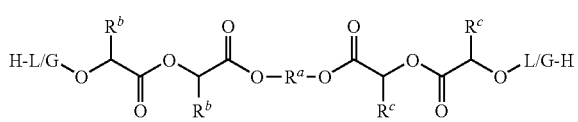

wherein:

$R^a$ is an alkane diradical comprising about 4 to about 8 carbon atoms;

$R^b$ is hydrogen or methyl with the proviso that both $R^b$ groups are identical;

$R^c$ is hydrogen or methyl with the proviso that both $R^c$ groups are identical;

each L/G independently comprises a lactide/glycolide copolymer segment;

the polymer has substantially no titratable carboxylic acid groups, and the polymer has a weight average molecular weight of from about 6 kD to about 200 kD.

Another type of low burst PLG copolymer, referred to herein as an "SFE-purified" PLG copolymer, as disclosed in the patent application filed herewith, is characterized as a PLG copolymer that has been purified by extraction with a supercritical fluid comprising carbon dioxide.

The PLG copolymer used in the inventive constant release copolymer composition can be of the PLGH type, i.e., having acidic carboxylic acid end groups on the molecular chains. The PLGH copolymer can be either purified or unpurified. When a purified PLGH of the PLGH(p) type is used, that is, a PLGH that has been purified by solvent precipitation as described in patent application U.S. Ser. No. 60/901,435, it has surprisingly been discovered by the inventors herein that addition of about 5 wt % of a PLG oligomer, for example, of a polylactide or of 65/35 poly(lactide-glycolide), either material having an average molecular weight of about 5-10 kDa, for example about 7 or 8 kDa, and lacking free carboxylic acid groups, when incorporated into a controlled release formulation of the Atrigel® type and implanted within the body tissues of a mammal, results in an increased linearity of the cumulative release profile of a contained bioactive agent, particularly in the later stages of the depot's lifetime in the body.

For example, referring to FIG. 1 (experimental procedure in Example 3), the release profiles of the small-molecule, anti-psychotic drug risperidone from depots formed using a flowable delivery system in rats are shown. The system is adapted to release risperidone over a period of about 28 days, and a zero-order, constant release rate would exhibit the ideal straight line as shown, with about 90% of the agent being released over the 28 day period. The control formulation, including 15% risperidone in copolymer PLGH(p) (a purified 80/20 PLGH, i.e., 80 mole % lactide, 20 mole % glycolide, and free carboxylic acid end groups) without any added PLG oligomer, in N-methylpyrrolidone (NMP) solution, exhibits a release profile (indicated by closed circles) with time points taken on the days indicated and the error bars representing plus or minus one standard error. As can be seen, for the first seven days after emplacement of the depot, the rate of release approximates the ideal rate without significant initial burst and without falling below the linear ideal. However, by day 14 the percentage of risperidone released is significantly below ideal. At day 21, the ideal rate shows a cumulative release of about 67% of total risperidone. Contrarily, the measured total cumulative release is only at about 52%, or 0.77 of ideal. By the end of the 28 day time period, the cumulative release is only about 58% of total risperidone, which is less than two thirds of the ideal cumulative release of 90%.

In contrast, the two release profiles indicated by the open and closed triangles depict the risperidone release versus time from inventive constant release copolymer compositions when 4.5% of 100% PLA (open triangles) or when 4.5% of 65/35 PLG (closed triangles), each of about 7-8 kDa average molecular weight and without free carboxylic acid groups is combined with the PLG copolymer. In both these compositions, the added PLG oligomer replaces by weight the PLG copolymer. In both compositions with the added hydrophobic PLG oligomer, the release profiles more closely approximate the ideal linear release profile, particularly during the time period near the end of release, at about 20-28 days. For example, the 100% PLA oligomer system provides a final release level of about 67% of total risperidone, and the 65/35 oligomer provides a final release level of about 82% of the total risperidone; both are substantially higher than in the system without added oligomer. Both inventive copolymer controlled release formulations are within experimental error of the ideal at the 21 day time point, whereas the cumulative release of the formulation lacking the oligomer additives is only about 0.65 of the ideal. It is clearly seen that the addition of the oligomers substantially eliminates the late-term drop-off in the rate of release of the risperidone from this controlled release formulation. The two curves indicated by open and closed squares signify compositions where the added PLG oligomer replaces solvent NMP; accordingly, the ratio of PLG oligomer to PLG copolymer is lower than in cases where the oligomer replaces by weight the copolymer, which may account for the greater deviation from ideality of these two compositions.

Figure 2:
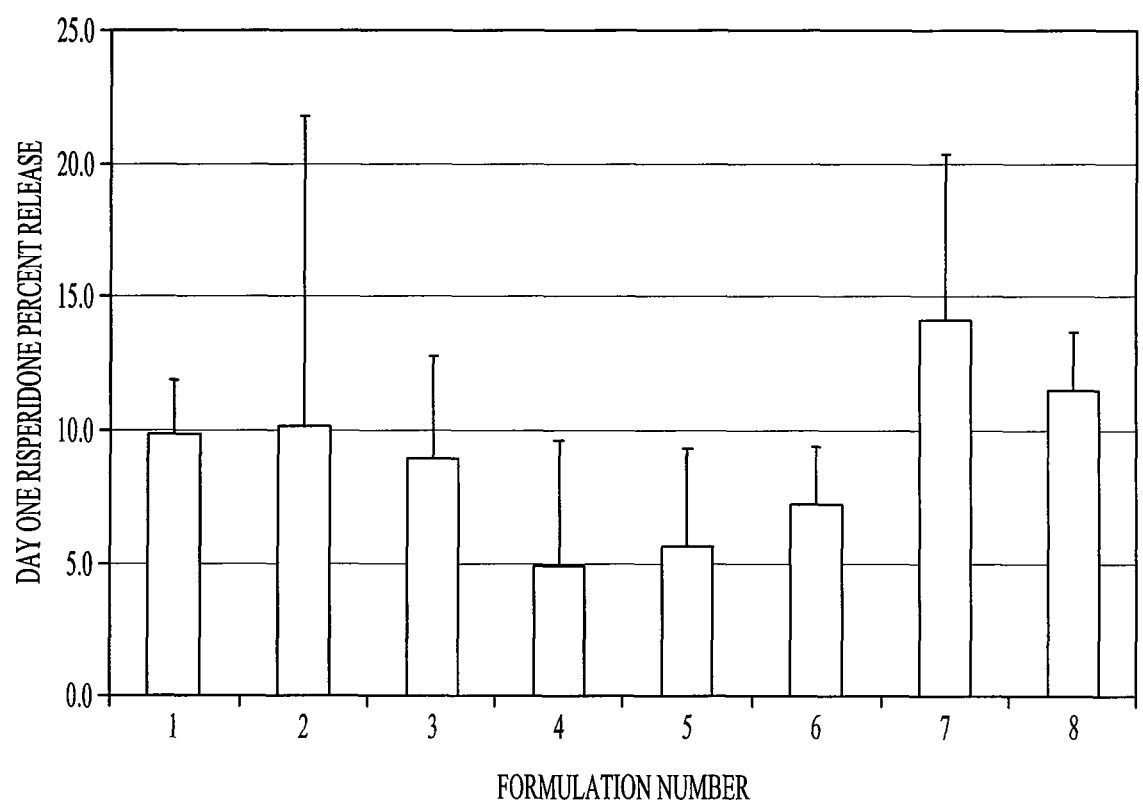
FIG. 2 has the Day One release data from the same study as described for FIG. 1 above.

FIG. 2 has the Day One release data from the same study with error bars of one standard error. This shows that the Day One release is comparable for all the formulations.

Figure 3:
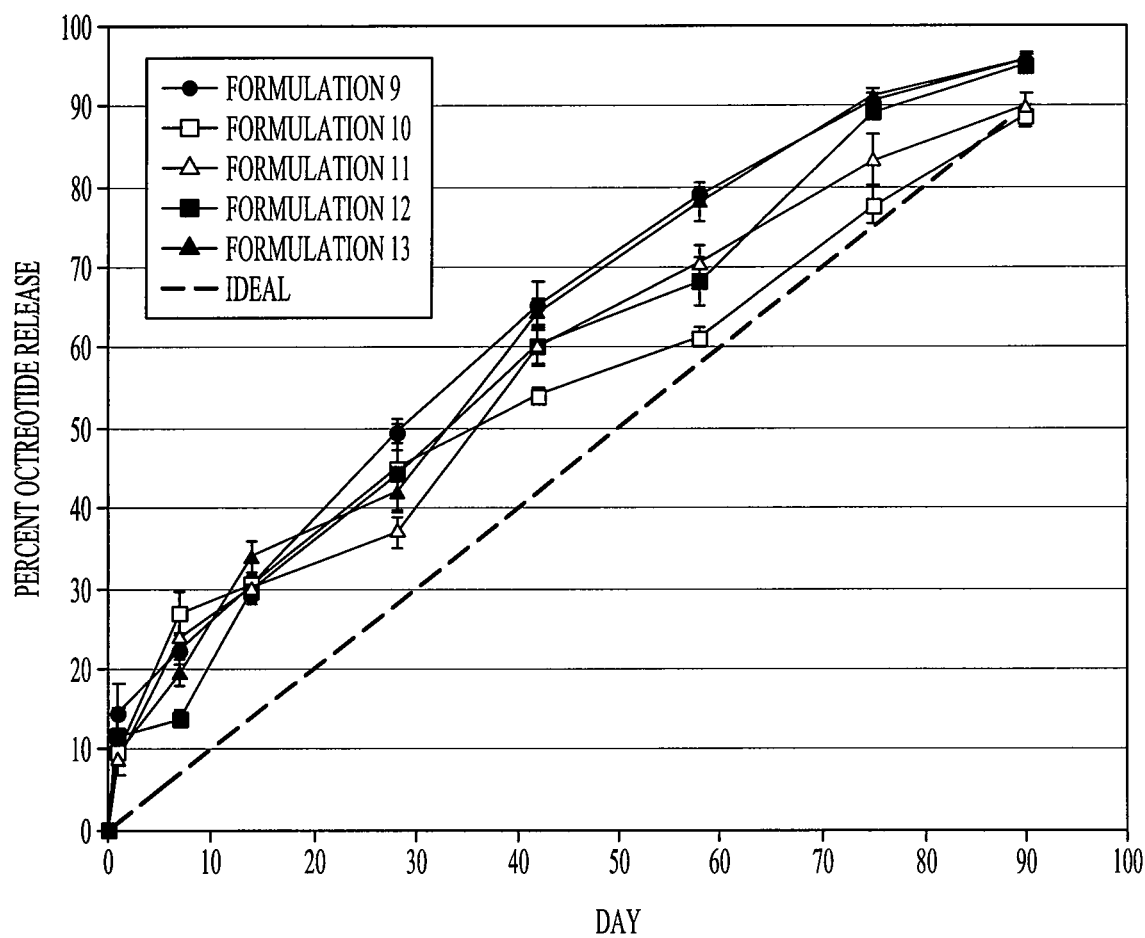
FIG. 3 shows data for the release of octreotide over a period of 90 days. The control formulation (closed circles) uses purified PLGH copolymer, in this case 85/15 PLGH(p), without any added PLG oligomer. The inventive formulations containing oligomers as additives are represented by the other symbols.

FIG. 3 (experimental procedure in Example 4) shows data for the release of octreotide, a peptide analog of molecular weight slightly greater than 1000, in rats from a controlled release formulation adapted to release the drug over a period of 90 days. Here again, the control formulation (closed circles) is composed of a purified PLGH copolymer, in this case 85/15 PLGH(p), without any added PLG oligomer. Similar to the risperidone formulation without added oligomer, the cumulative release curve deviates significantly from the ideal, which is a straight line between 0% at 0 days and about 90% at 90 days. After some initial burst between 0 and about 2 days, the control release profile reaches a maximum variance above the ideal release line at about 40 days, then tapers off to a lower release rate (lower slope of the line) late in the period, particularly between about 70-90 days. The other four lines represent various inventive compositions comprising a PLG copolymer and a PLG oligomer. The open squares and open triangles represent the release profiles of the octreotide from 85/15 PLGH(p) formulations including 4.5% PLA of about 7 kDa average molecular weight and lacking carboxylic acid end groups, wherein the total PLG copolymer concentrations in NMP are respectively 50% and 45%. The closed black squares and closed triangles represent the release profiles of the octreotide from PLGH(p) copolymer formulations comprising 4.5% 65/35 PLG oligomers of less than 10 kDa molecular weight and lacking carboxylic end groups, wherein the total PLG copolymer concentrations in NMP are respectively 50% and 45%. As can be seen, all the curves depicting release from formulations that include the inventive copolymer compositions including the oligomers more closely approximate the linear ideality. In this system, the PLA oligomer appears to be even more effective at the later period, especially from about 60 to 90 days after emplacement of the depot in the test animal, than does the 65/35 PLG oligomer with respect to the cumulative release profile. This becomes even more apparent if one accounts for the initial burst and defines the linear ideality as starting at about 10% total release at 2 days instead of at 0% total release at 0 days.

Figure 4:
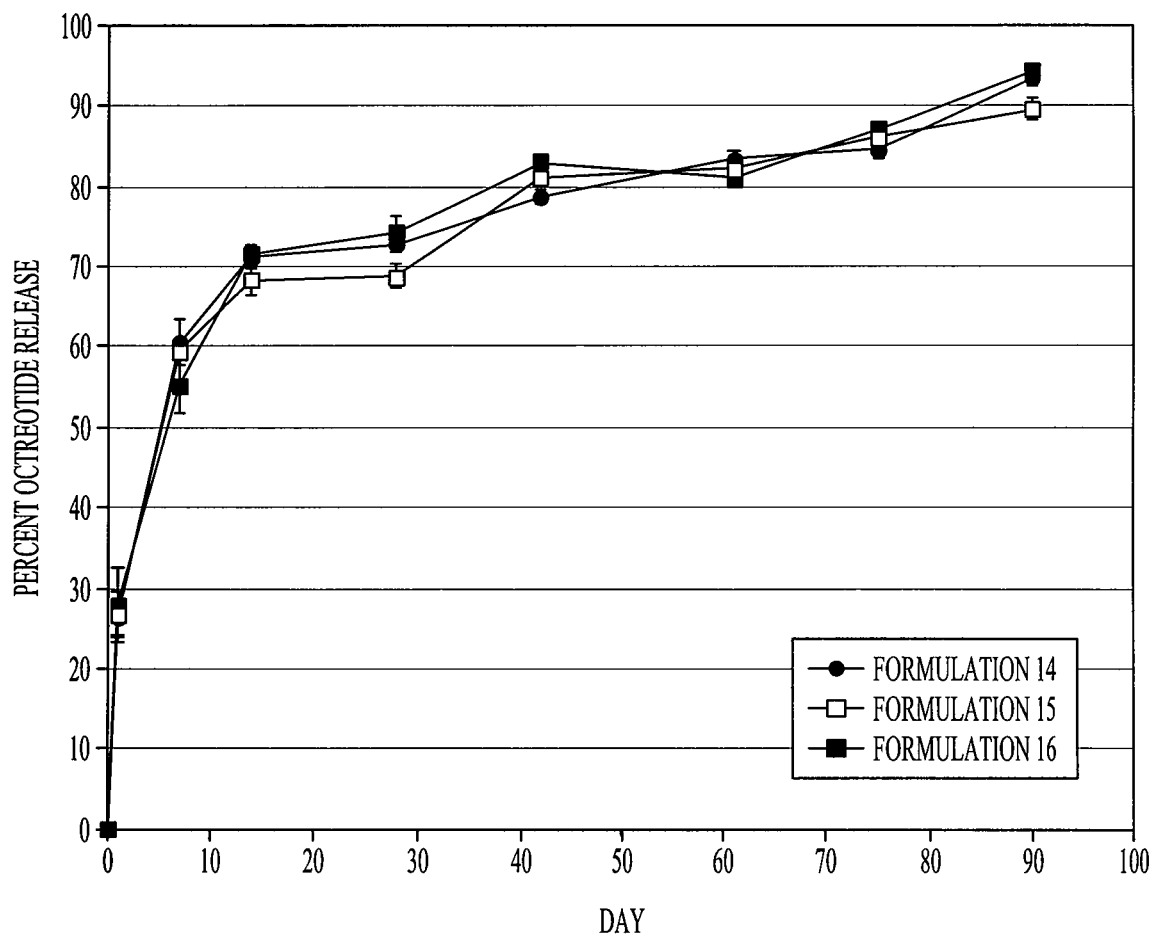
FIG. 4 shows a 90-day release profile of octreotide in rats from a control and two inventive copolymer compositions, comparable to the study shown in FIG. 3, except using an unpurified PLGH copolymer.

FIG. 4 (experimental procedure in Example 4) shows a 90-day release profile of octreotide in rats from a control and two inventive copolymer compositions, comparable to the study shown in FIG. 3, except using an unpurified PLGH copolymer. Here the use of the unpurified copolymer appears to overwhelm the modification of the release profile by addition of the oligomers.

Figure 5:
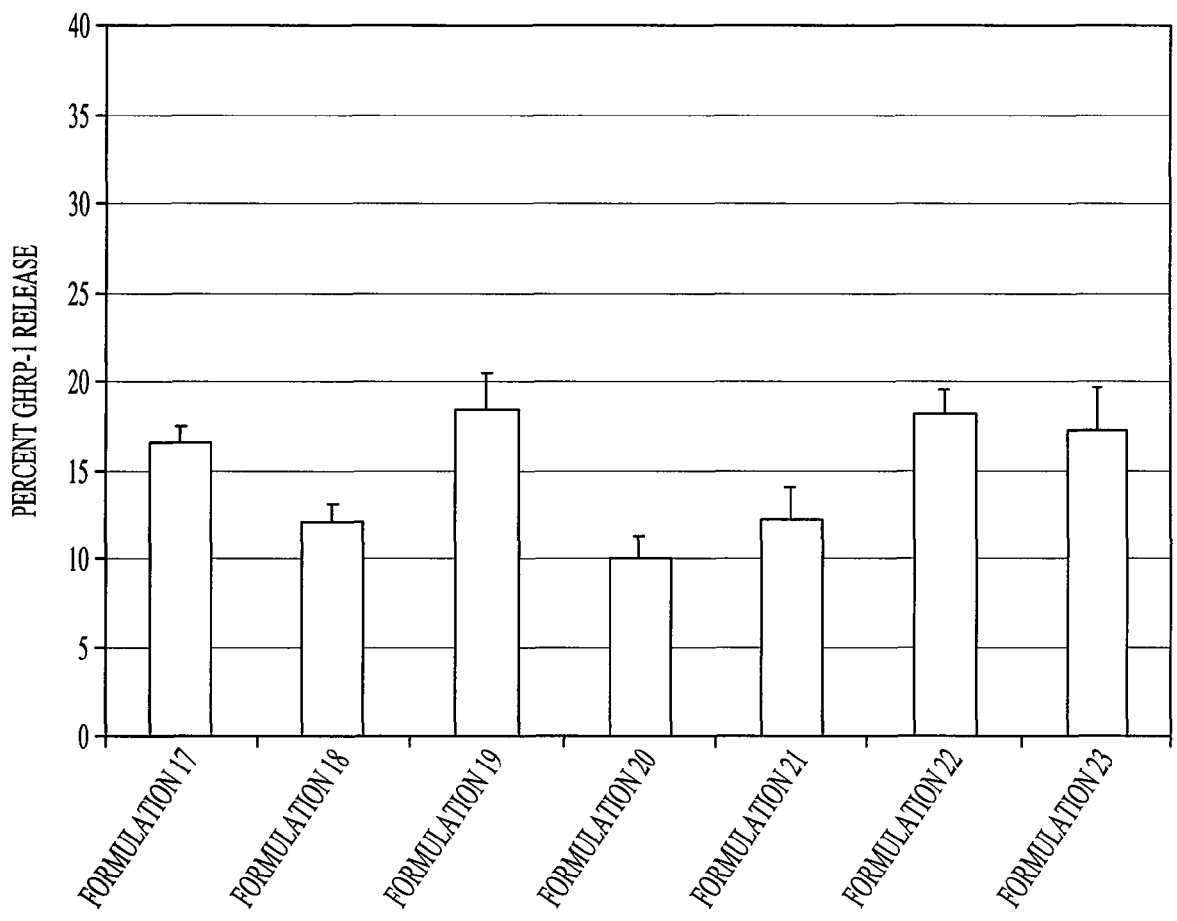
FIG. 5 shows Day One release data for GHRP-1 from depots of controlled release formulations emplaced in rats.

FIG. 5 (experimental procedure in Example 5) shows Day One release data for GHRP-1 from depots of controlled release formulations emplaced in rats. The formulations include a control containing only a purified 75/25 PLGH and six test systems, each containing a copolymer system composed of the 75/25 PLGH(p) and a PLG oligomer, such as a PLA oligomer, 65/35 PLG oligomer or 65/35 PLGH oligomer. The Day One releases for all of these formulations are comparable.

Figure 6:
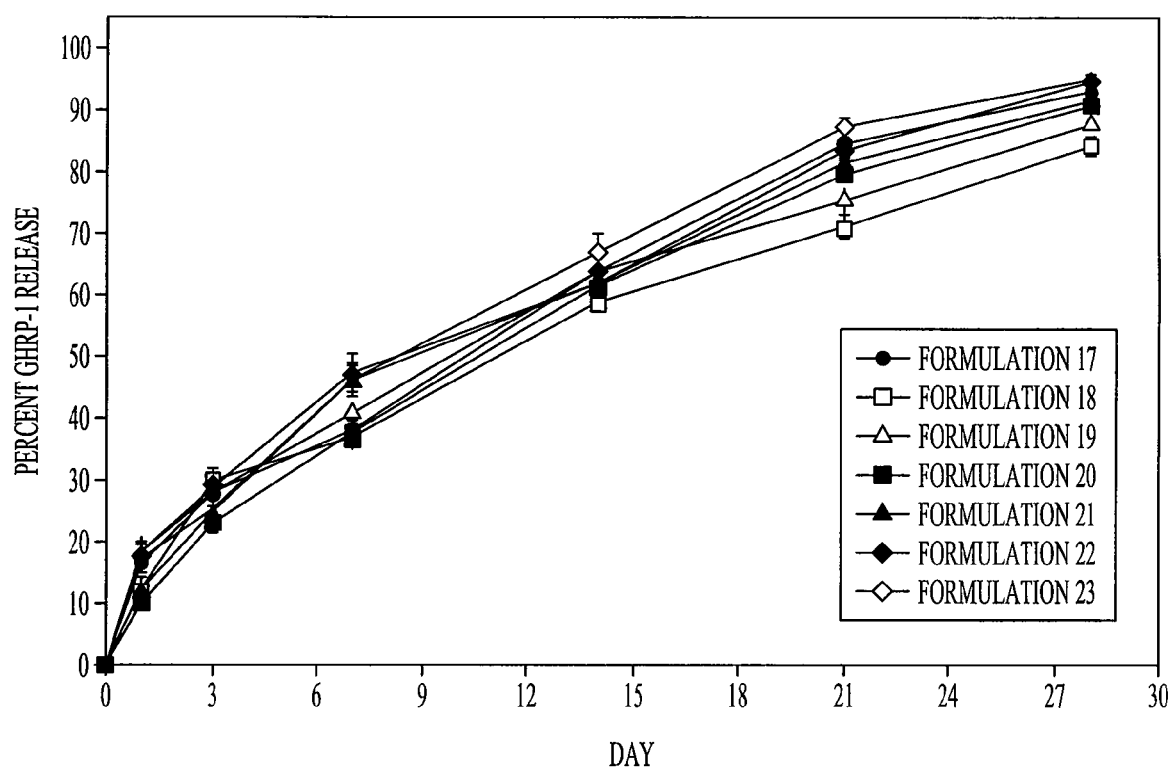
FIG. 6 shows 28-day release profiles for GHRP-1 from controlled release depots emplaced in rats for the same set of formulations as in FIG. 5. The control formulation (closed circles) uses purified PLGH copolymer, in this case 75/25 PLGH(p), without any added PLG oligomer. The inventive formulations containing oligomers as additives are represented by the other symbols.

FIG. 6 shows 28-day release profiles for GHRP-1 from controlled release depots emplaced in rats for the same set of formulations as in FIG. 5. The two formulations with the added PLA oligomer exhibited slower release than the other formulations past day 14.

Figure 7:
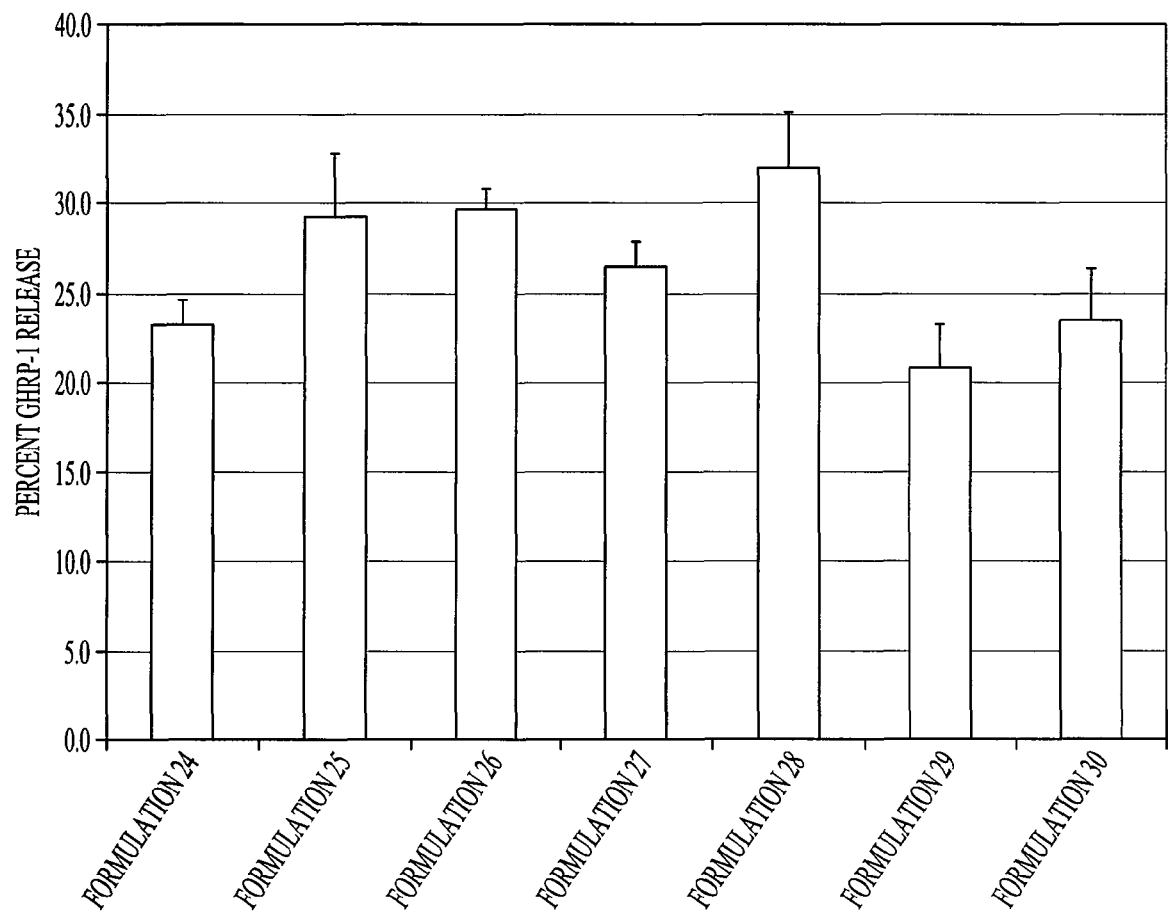
FIG. 7 shows Day One release data for GHRP-1 from depots of controlled release formulations emplaced in rats. The formulations include a control containing only an unpurified 75/25 PLGH and six inventive formulations, each containing a copolymer system of the unpurified 75/25 PLGH and a PLG oligomer, such as a PLA oligomer, 65/35 PLG oligomer or 65/35 PLGH oligomer.

FIG. 7 (experimental procedure in Example 5) shows Day One release data for GHRP-1 from depots of controlled release formulations emplaced in rats. The formulations include a control containing only an unpurified 75/25 PLGH and six test systems, each containing a copolymer system of the unpurified PLGH and a PLG oligomer, such as a PLA oligomer, 65/35 PLG oligomer or 65/35 PLGH oligomer. This shows that the Day One release from all these formulations is comparable. All of the Day One GHRP-1 releases with unpurified PLGH base polymer (FIG. 7) are higher than the Day One GHRP-1 releases with purified PLGH base polymer (FIG. 5).

Figure 8:
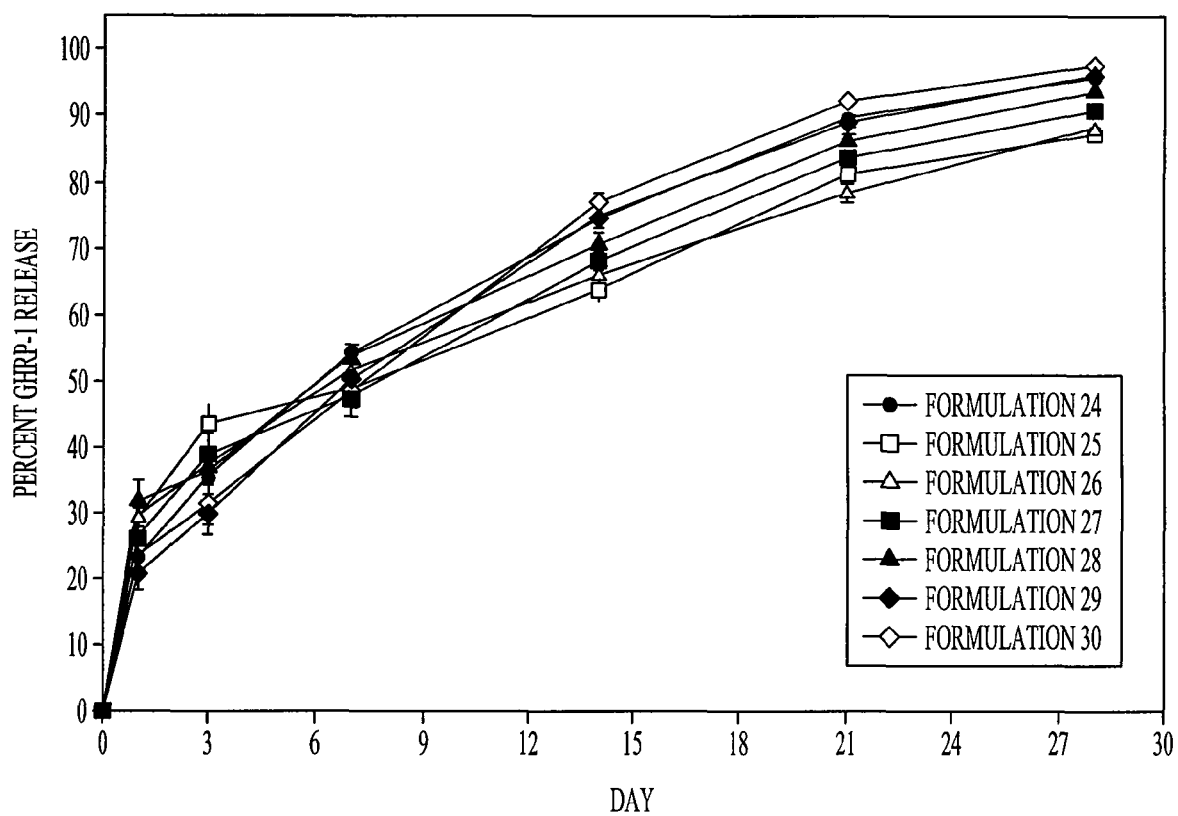
FIG. 8 shows 28-day release profiles for GHRP-1 from controlled release depots emplaced in rats for the same set of formulations as in FIG. 7. The control formulation (closed circles) uses unpurified PLGH copolymer without any added PLG oligomer. The inventive formulations containing oligomers as additives are represented by the other symbols.

FIG. 8 shows 28-day release profiles for GHRP-1 from controlled release depots emplaced in rats for the same set of formulations as in FIG. 7 with unpurified 75/25 PLGH base polymer. It can be seen that in four of the test samples, incorporating a 7 kDa average molecular weight 100 mole % poly-lactide oligomer (PLA) or an 8 kDa average molecular weight 65 mole % lactide/35 mole % glycolide oligomer (65/35 PLG) (open squares, open triangles, closed squares and closed triangles), the release of the GHRP-1 is more linear over the time period immediately following the initial burst (starting at 3 days post-emplacement) through 28 days. Once again, the leveling effect of added oligomer is seen. In the two cases where the added PLG oligomer is an acidic PLGH oligomer (closed diamonds and open diamonds), the effect is less pronounced.

These experimental data obtained using a variety of different bioactive agents with varying properties indicate that the release control obtained through use of the inventive copolymer systems is a general phenomenon, not limited to a particular agent, although the quantitative impact can vary among different bioactive agents. The inventive copolymer composition is adapted to control non-linearity of release from controlled release formulation such as those of the Atrigel® type, and, especially when used with a low burst PLG copolymer such as a PLGH(p), provides for substantially more linearity of release, a closer approach to zero-order release kinetics, than do art copolymer systems.

While not wishing to be bound by theory, it is likely that the addition of the oligomers to the formulations modify the polymer degradation rate particularly at later time points and the polymer degradation in turn affects the drug release. There appears to be a complex interplay of various factors involved. It is noteworthy that addition of a PLA oligomer to a formulation with risperidone and 75/25 PLGH polymer actually increases the rate of risperidone release in the later portions of the 28 day release (FIG. 1) while addition of the same PLA oligomer to a formulation with octreotide and 85/15 PLGH polymer decreases the rate of octreotide release in the later portions of the 90 day release (FIG. 3).

It is understood that many parameters of this copolymer system can be varied by the skilled artisan to adjust the properties of the copolymer system and of a controlled release formulation incorporating the system. For example, the relative proportion of the PLG oligomer in the constant release copolymer composition, and the molecular properties of the oligomer as well as of the PLG copolymer, can be varied to achieve a particular desired result in terms of the release profile for a particular drug. As the molecular properties of the bioactive agents themselves vary depending upon the nature of the agent in question, for a given agent the parameters can be adjusted by the skilled artisan using routine experimentation to provide the desired release profile. For example, the hydrophobicity of the oligomer and of the PLG copolymer can be adjusted by altering the relative proportions of lactide and glycolide units. The molecular weights of the PLG copolymer and, to a lesser extent, of the PLG oligomer, can be varied.

Typical molecular weights of the PLG copolymer can be between about 10 kDa and 50 kDa. For a low burst PLG copolymer, for example a PLG(p) copolymer, the weight average molecular weight can be about 10-50 kDa with a polydispersity index of about 1.4-2.0, having separated therefrom a copolymer fraction characterized by a weight average molecular weight of about 4-10 kDa and a polydispersity index of about 1.4 to 2.5. For an SFE-purified PLG copolymer, the weight average molecular weight can be about 28-35 kDa with a polydispersity index of about 1.4-1.5.

The solvent used in the controlled release formulation can be changed, as can routinely be done by a person of ordinary skill in the art without undue experimentation, to adjust the controlled release properties of the formulation.

The solvent has at least a small degree of solubility in body fluids. The solvent can be completely soluble in the body fluids. The organic solvent can be N-methylpyrrolidone, N,N-dimethylformamide, N,N-dimethylacetamide, dimethylsulfoxide, polyethylene glycol 200, polyethylene glycol 300, or methoxypolyethylene glycol 350, or a mixture thereof.

Various embodiments of the inventive copolymer compositions can also be used with controlled release formulations other than of the Atrigel® type, in which other solvents may be used. For example, embodiments of the constant release copolymer composition of the invention can be used with controlled release formulations including microparticles, nanoparticles, emulsions, solid monolithic implants, and the like.

To further adjust the system properties, the concentrations of the drug and of the inventive PLG copolymer/oligomer composition in the solvent can be varied, and the amount of the formulation emplaced within the patient can also be adjusted. Furthermore, biodegradable polyesters other than poly(lactide-glycolide), such as, for example, poly(caprolactone) and its copolymers, can be components of a controlled release formulation also incorporating the inventive copolymer composition.

The controlled release formulation can be prepared by combining the PLG copolymer, the PLG oligomer, the bioactive agent, and the organic solvent. For example, the PLG copolymer and the oligomer can be premixed as solids, then dissolved in the solvent, followed by addition of the bioactive agent immediately prior to emplacement of the formulation in the patient. The formulation can be sterilized by means known in the art, for example, gamma irradiation or by electron beam radiation. A controlled release formulation can be made up by dissolving the inventive copolymer system in an organic solvent that is at least somewhat soluble in body fluids at a suitable concentration and adding a medically indicated bioactive agent.

Various embodiments of the invention further provide methods of administering a bioactive agent to a patient over a prolonged period of time, wherein a substantially constant rate of release of the bioactive agent is achieved, the method involving administering to the patient an embodiment of the inventive controlled release formulation of the bioactive agent. The depot can be emplaced at any suitable position within the patient's body tissues, for example, subcutaneously adjacent to the abdominal wall, or within the abdominal cavity, within a muscle, within an eyeball, within a cerebral ventricle, or the like. Typically a depot of the Atrigel® type is emplaced with a hypodermic syringe, but other devices or methods as are known in the art can be employed. Various embodiments of the invention provide kits adapted for use in administration of embodiments of inventive copolymer compositions incorporating bioactive agents for controlled release of the agent in body tissues of a patient in need thereof.

The bioactive agent contained within the controlled release formulation including an inventive copolymer system is adapted to treat the malcondition for which it is administered. For example, the agent can be leuprolide when the malcondition is prostate cancer; octreotide when the malcondition is acromegaly, risperidone when the malcondition is psychosis, an analgesic when the malcondition is pain, and so forth. Formulations adapted to release the bioactive agent over various periods of time can be used as medically indicated. In the palliative treatment of prostate cancer where suppression of testosterone biosynthesis is indicated, typically for the remaining lifetime of the patient, a long term formulation such as a formulation adapted to release the bioactive agent leuprolide for a period of 6 months or more can be used. This serves to reduce the pain and inconvenience of multiple depot emplacements. Alternatively, in treatment of malconditions where such prolonged release is not indicated, for example in the treatment of post-operative pain, a formulation can be used that is adapted to release the analgesic agent, for example a COX-2 inhibitor, for a shorter period, such as for 30 days.

EXAMPLES

Example 1

Polymer and Oligomer Synthesis

All polymers and oligomers used in the examples were prepared by bulk copolymerization of DL lactide and glycolide using tin II 2-ethylhexanoate (stannous octoate) as the catalyst. PLG oligomers were prepared using 1,6 hexanediol as the initiator and a reaction temperature of approximately 145° C. The PLGH polymers and oligomer were prepared using glycolic acid as the initiator and a reaction temperature of approximately 165° C. The ratio of initiator to comonomers was varied to change the molecular weight of the polymer. The higher this ratio, the lower the molecular weight of the polymer. The reactions were run for approximately 2.5 hours. This was followed by an approximately 2 hour period at the same temperature of pulling a vacuum on the reaction mixture to remove unreacted monomer. The molten polymer was then removed from the reactor and allowed to cool in dry conditions.

Unless otherwise indicated, all molecular weights described in this document are weight average molecular weights obtained by gel permeation chromatography (GPC) using a Polymer Laboratories, PLgel MIXED-D, 5 μm, 30 cm×7.5 mm GPC column at 40° C. with tetrahydrofuran as the solvent. A volume of 50 μL of an approximately 0.5% (w/v) polymer in tetrahydrofuran was injected. The flow rate was 1 ml/min. Narrow molecular weight distribution polystyrene molecular weight standards were used to create a calibration curve.

Two samples of PLG oligomers were prepared as described: 100 mole % lactide, and 65 mole % lactide/35 mole % glycolide, both using a hexane-1,6-diol core such that the product oligomers possessed terminal hydroxyl groups with substantially no free carboxylic acid groups. The 100 mole % polylactide had an average molecular weight of 7 kDa, and the 65/35 lactide-glycolide oligomer had an average molecular weight of 8 kDa. One 65/35 PLGH oligomer with a molecular weight of 9 kDa was prepared as described.

Example 2

Release Studies in Rats

All rat preclinical studies were conducted in Sprague-Dawley rats. Five rats per Test Article per time point were injected subcutaneously under full anesthesia in the dorsal thoracic (DT) region with approximately 100 mg of the Test Article. Each injection weight was recorded.

During the course of the study, the animals were observed for overt toxicity and any existing test site abnormalities, including redness, bleeding, swelling, discharge, bruising and Test Article extrusion at the injection site were observed and recorded. In addition, injection weights were recorded at administration and body weights were taken and recorded at administration and at termination.

At selected time points, five rats per Test Article were terminated with carbon dioxide and the implants were retrieved.

Each retrieved implant was then analyzed by HPLC for the amount of active remaining in the implant. This was then subtracted from the amount of active present in the injection weight to determine the cumulative percent release.

Example 3

Rate of Release of Risperidone in Rats from Atrigel Depots Containing PLG Oligomers A variety of delivery systems were prepared by mixing an 80/20 PLGH base polymer (purified or not purified) with N-methyl-pyrrolidone and optionally one of the PLG oligomers to form a solution. The delivery systems are described in Table 1. These delivery systems were filled into syringe. The delivery systems were gamma irradiated at 18-28 kGray either in bulk or in the syringe. A second set of syringes was filled with risperidone powder. The contents of a delivery system syringe and a risperidone syringe were mixed by coupling the syringes and passing the syringe contents back and forth to prepare a final formulation of 15% (weight/weight) risperidone.

TABLE 1

Composition of various PLG copolymer/oligomer Delivery Systems tested with Risperidone in a 28 Day Study

| Delivery System Number | Base Polymer | % Base Polymer | Additive | % Additive | % NMP |
|---|---|---|---|---|---|
| 1 | 80/20 PLGHp | 45 | None | 0 | 55 |
| 2 | 80/20 PLGH (unpurified) | 45 | None | 0 | 55 |
| 3 | 80/20 PLGHp | 45 | PLA | 4.5 | 50.5 |
| 4 | 80/20 PLGHp | 40 | PLA | 4.5 | 55.5 |
| 5 | 80/20 PLGHp | 45 | 65/35 PLG | 4.5 | 50.5 |
| 6 | 80/20 PLGHp | 40 | 65/35 PLG | 4.5 | 55.5 |

These formulations were then used in a 28 day rat study as described in Example 2. Table 2 gives the cumulative percent release for the time points tested for an ideal linear release with 90% released on day 28. Tables 3 through 8 give the percent release data for 15% risperidone mixed with delivery systems 1 through 6, respectively. The tables include the mean value, standard deviation (SD) and standard error (SE) for each time point. FIG. 1 shows these results graphically with error bars of plus or minus the standard error.

TABLE 2

Percent release vs. time for ideal linearity

| Day | Ideal |
|---|---|
| 0 | 0 |
| 1 | 3.2 |
| 3 | 9.6 |
| 7 | 22.5 |
| 14 | 45.0 |
| 21 | 67.5 |
| 28 | 90.0 |

TABLE 3

Percent release vs. time for formulation 1 (purified PLGHp copolymer with no added oligomer)

| Day | % Release | SD | SE |
|---|---|---|---|
| 0 | 0 | 0 | 0 |
| 1 | 9.9 | 4.5 | 2.0 |
| 3 | 8.6 | 8.2 | 3.6 |
| 7 | 25.7 | 9.8 | 4.4 |
| 14 | 38.5 | 9.5 | 4.2 |

TABLE 3-continued

Percent release vs. time for formulation 1
(purified PLGHp copolymer with no added oligomer)

| Day | % Release | SD | SE |
|---|---|---|---|
| 21 | 51.7 | 10.0 | 4.5 |
| 28 | 57.8 | 6.0 | 2.7 |

TABLE 4

Percent release vs. time for formulation 2
(unpurified PLGH copolymer with no added oligomer)

| Day | % Release | SD | SE |
|---|---|---|---|
| 0 | 0 | 0 | 0 |
| 1 | 10.1 | 26.0 | 11.6 |
| 3 | 14.8 | 27.9 | 12.5 |
| 7 | 20.2 | 18.3 | 8.2 |
| 14 | 37.2 | 15.3 | 6.8 |
| 21 | 51.6 | 23.6 | 10.6 |
| 28 | 46.6 | 9.9 | 4.4 |

TABLE 5

Percent release vs. time for formulation 3
(PLGHp with added PLA)

| Day | % Release | SD | SE |
|---|---|---|---|
| 0 | 0 | 0 | 0 |
| 1 | 8.9 | 8.5 | 3.8 |
| 3 | 12.7 | 12.4 | 5.5 |
| 7 | 25.4 | 10.1 | 4.5 |
| 14 | 32.6 | 15.0 | 6.7 |
| 21 | 50.0 | 18.2 | 8.1 |
| 28 | 50.0 | 4.3 | 1.9 |

TABLE 6

Percent release vs. time for formulation 4
(PLGHp with added PLA)

| Day | % Release | SD | SE |
|---|---|---|---|
| 0 | 0 | 0 | 0 |
| 1 | 4.9 | 10.5 | 4.7 |
| 3 | 3.9 | 21.8 | 9.7 |
| 7 | 24.7 | 13.5 | 6.0 |
| 14 | 31.0 | 9.5 | 4.3 |
| 21 | 64.7 | 16.0 | 7.1 |
| 28 | 66.9 | 12.2 | 5.4 |

TABLE 7

Percent release vs. time for formulation 5
(PLGHp with added 65/35 PLG)

| Day | % Release | SD | SE |
|---|---|---|---|
| 0 | 0 | 0 | 0 |
| 1 | 5.6 | 8.2 | 3.7 |
| 3 | 6.8 | 17.3 | 7.7 |
| 7 | 24.5 | 11.2 | 5.0 |
| 14 | 35.5 | 19.3 | 8.6 |
| 21 | 54.0 | 13.2 | 5.9 |
| 28 | 57.5 | 7.3 | 3.3 |

TABLE 8

Percent release vs. time for formulation 6
(PLGHp with added 65/35 PLG)

| Day | % Release | SD | SE |
|---|---|---|---|
| 0 | 0 | 0 | 0 |
| 1 | 7.2 | 4.9 | 2.2 |
| 3 | 27.3 | 7.9 | 3.6 |
| 7 | 20.7 | 7.6 | 3.4 |
| 14 | 38.6 | 8.6 | 3.9 |
| 21 | 70.3 | 13.9 | 6.2 |
| 28 | 82.2 | 11.1 | 4.9 |

Two 15% risperidone formulations using the 65/35 PLGH oligomer were prepared and tested in the rat model as described in Example 2, but only one day release was determined. Table 9 gives the delivery system compositions. Table 10 gives the release data. FIG. 2 shows the day one release data for the all the risperidone formulations in this example with error bars of plus one standard error.

TABLE 9

Composition of various PLG copolymer/PLGH oligomer Delivery Systems tested with Risperidone in a One Day Study

| Delivery System Number | Base Polymer | % Base Polymer | Additive | % Additive | % NMP |
|---|---|---|---|---|---|
| 7 | 80/20 PLGHp | 45 | 65/35 PLGH | 4.5 | 50.5 |
| 8 | 80/20 PLGHp | 40 | 65/35 PLGH | 4.5 | 55.5 |

TABLE 10

Day one percent release for formulations 7 and 8
(containing 65/35 PLGH oligomer)

| Formulation # | % Release | SD | SE |
|---|---|---|---|
| 7 | 14.1 | 13.9 | 6.2 |
| 8 | 11.5 | 4.9 | 2.2 |

Example 4

Rate of Release of Octreotide in Rats from Atrigel Depots Containing PLG Oligomers These investigations were performed using what was termed octreotide drug powder (ODP). ODP is the product of the lyophilization of an aqueous 1:1 molar ratio of octreotide acetate and citric acid solution. This powder was then hand filled in syringes for combination with various Delivery Systems that had been irradiated in the 18-28 kiloGray range. Each formulation contained 12% w/w ODP after mixing the contents of the two syringes.

Table 11 presents the delivery systems that were studied in which a purified 85/15 PLGH is the base polymer. These octreotide formulations were then tested in rats as described in Example 2 with time points of 1, 7, 14, 28, 42, 60, 76 and 90 days. Results are shown in FIG. 3 with error bars of plus or minus one standard error.

TABLE 11

Composition of Purified PLG H/oligomer Delivery Systems tested with Octreotide in a 90 Day Study

| Delivery System Number | Base Polymer | % Base Polymer | Additive | % Additive | % NMP |
|---|---|---|---|---|---|
| 9 | 85/15 PLGHp | 50 | None | 0 | 50 |
| 10 | 85/15 PLGHp | 50 | PLA | 4.5 | 45.5 |
| 11 | 85/15 PLGHp | 45 | PLA | 4.5 | 50.5 |
| 12 | 85/15 PLGHp | 50 | 65/35 PLG | 4.5 | 45.5 |
| 13 | 85/15 PLGHp | 45 | 65/35 PLG | 4.5 | 50.5 |

Table 12 presents the delivery systems that were studied in which an unpurified 85/15 PLGH is the base polymer. These octreotide formulations were then tested in rats as described in Example 2 with time points of 1, 7, 14, 28, 42, 60, 76 and 90 days. Results are shown in FIG. 4 with error bars of plus or minus one standard error.

TABLE 12

Composition of Unpurified PLGH/oligomer Delivery Systems tested with Octreotide in a 90 Day Study

| Delivery System Number | Base Polymer | % Base Polymer | Additive | % Additive | % NMP |
|---|---|---|---|---|---|
| 14 | 85/15 PLGH | 50 | None | 0 | 50 |
| 15 | 85/15 PLGH | 50 | PLA | 4.5 | 45.5 |
| 16 | 85/15 PLGH | 50 | 65/35 PLG | 4.5 | 45.5 |

Example 5

Rate of Release of GHRP-1 in Rats from Atrigel® Depots Containing PLG Oligomers

A variety of delivery systems were prepared by mixing a 75/25 PLGH base polymer (purified or not purified) (21 kDa) with N-methyl-pyrrolidone and optionally one of the PLG oligomers to form a solution. The delivery systems are described in Tables 13 and 14. These delivery systems were filled into syringe. The delivery systems were gamma irradiated at 18-28 kGray either in bulk or in the syringe. A second set of syringes was prepared by lyophilization of an aqueous solution of GHRP-1 acetate, citric acid and acetic acid. The contents of a delivery system syringe and a GHRP-1 syringe were mixed by coupling the syringes and passing the syringe contents back and forth to prepare a final formulation of 10% (weight/weight) GHRP-1 acetate, 1.1% (weight/weight) citric acid and 1.4% % (weight/weight) acetic acid.

Table 13 presents the delivery systems that were studied in which a purified 75/25 PLGH is the base polymer. These GHRP-1 formulations were then tested in rats as described in Example 2 with time points of 1, 3, 7, 14 and 28 days. Results are shown in FIGS. 5 and 6 with error bars of one standard error. FIG. 5 presents the day one release data. FIG. 6 presents the cumulative release minus day one release for the subsequent time points. This is to clarify the differences in release rate at these later time points.

TABLE 13

Composition of Purified PLG H/oligomer Delivery Systems tested with GHRP-1 in a 28 Day Study

| Delivery System Number | Base Polymer | % Base Polymer | Additive | % Additive | % NMP |
|---|---|---|---|---|---|
| 17 | 75/25 PLGHp | 50 | None | 0 | 50 |
| 18 | 75/25 PLGHp | 50 | PLA | 4.5 | 45.5 |
| 19 | 75/25 PLGHp | 45.5 | PLA | 4.5 | 50 |
| 20 | 75/25 PLGHp | 50 | 65/35 PLG | 4.5 | 45.5 |
| 21 | 75/25 PLGHp | 45.5 | 65/35 PLG | 4.5 | 50 |
| 22 | 75/25 PLGHp | 50 | 65/35 PLGH | 4.5 | 45.5 |
| 23 | 75/25 PLGHp | 45.5 | 65/35 PLGH | 4.5 | 50 |

Table 14 presents the delivery systems that were studied in which an unpurified 75/25 PLGH is the base polymer. These GHRP-1 formulations were then tested in rats as described in Example 2 with time points of 1, 3, 7, 14 and 28 days. Results are shown in FIGS. 5 and 6 with error bars of one standard error. FIG. 7 presents the day one release data. FIG. 8 presents the cumulative release minus day one release for the subsequent time points. This is to clarify the differences in release rate at these later time points.

TABLE 14

Composition of Unpurified PLG H/oligomer Delivery Systems tested with GHRP-1 in a 28 Day Study

| Delivery System Number | Base Polymer | % Base Polymer | Additive | % Additive | % NMP |
|---|---|---|---|---|---|
| 24 | 75/25 PLGH | 50 | None | 0 | 50 |
| 25 | 75/25 PLGH | 50 | PLA | 4.5 | 45.5 |
| 26 | 75/25 PLGH | 45.5 | PLA | 4.5 | 50 |
| 27 | 75/25 PLGH | 50 | 65/35 PLG | 4.5 | 45.5 |
| 28 | 75/25 PLGH | 45.5 | 65/35 PLG | 4.5 | 50 |
| 29 | 75/25 PLGH | 50 | 65/35 PLGH | 4.5 | 45.5 |
| 30 | 75/25 PLGH | 45.5 | 65/35 PLGH | 4.5 | 50 |

Concentrations, amounts, percentages, time periods, etc., of various components or use or effects of various components of this invention, including but not limited to the flowable composition, implants, indications of reduction in malcondition symptoms, and treatment time periods, are often presented in a range or baseline threshold format throughout this patent document. The description in range or baseline threshold format is merely for convenience and brevity and should not be construed as an inflexible limitation on the scope of the invention. Accordingly, the description of a range or baseline threshold should be considered to have specifically disclosed all the possible subranges as well as individual numerical values within that range or above that baseline threshold. For example, description of a release profile of about 20-28 days should be considered to have specifically disclosed subranges, such as 21 to 27 days, 22 to 26 days, 23 to 25 days, etc., as well as individual numbers within that range, such as 21 days, 23 days, 26 days, etc. This construction applies regardless of the breadth of the range or baseline threshold and in all contexts throughout this disclosure.

All publications, patents, and patent documents are incorporated by reference herein, as though individually incorporated by reference. While the invention has been described and exemplified in sufficient detail for those skilled in this art to make and use it, various alternatives, modifications, and improvements will be apparent to those skilled in the art without departing from the spirit and scope of the claims.

What is claimed is:

1. A controlled release formulation comprising a constant release copolymer composition, a bioactive agent, and an organic solvent having at least a slight solubility in body fluid wherein the constant release copolymer composition comprises a mixture of a PLG copolymer and a PLG oligomer, the PLG copolymer is a poly(lactide-glycolide) copolymer without a core diol unit, the poly(lactide-glycolide) copolymer having a monomer molar proportion of up to 100 mole % lactide to 100 mole % glycolide, the PLG oligomer is a poly(lactide-glycolide) oligomer with a core diol unit, the PLG oligomer having a monomer molar proportion of up to 100 mole % lactide, the PLG oligomer having a weight average molecular weight of about 5 to 10 kDa, and the PLG oligomer being present in about 2 wt % to about 10 wt % of the total weight of the PLG copolymer and PLG oligomer.

2. The controlled release formulation of claim 1 wherein the organic solvent is N-methylpyrrolidone, dimethylacetamide, dimethylformamide, dimethylsulfoxide, or a polyethyleneglycol.

3. The controlled release formulation of claim 1 wherein the bioactive agent comprises a peptide, a protein, a steroid, a prostaglandin, a hormone or hormone regulating substance, an anti-psychotic, an anti-inflammatory, an analgesic or a nucleic acid.

4. The controlled release formulation of claim 1 comprising as a bioactive agent risperidone, octreotide, leuprolide, or GHRP-1.

5. The controlled release formulation of claim 1 wherein the weight average molecular weight of the PLG oligomer is about 7 to about 8 kDa.

6. The controlled release formulation of claim 1 wherein the PLG oligomer comprises more than about 60% lactide residues on a molar basis.

7. A method of preparing the controlled release formulation of claim 1 for a bioactive agent comprising combining a PLG oligomer having a weight average molecular weight of about 5 to about 10 kDa, and a PLG copolymer, to provide a constant release copolymer composition, then forming the controlled release formulation by combining the constant release copolymer composition with an organic solvent having at least a slight solubility in body fluids and with the bioactive agent.

8. The method of claim 7 wherein the PLG copolymer is a low burst copolymer.

9. The method of claim 7 wherein the PLG copolymer is a PLG(p), a core diol PLG, or a SFE-purified PLG.

10. The method of claim 7 wherein the PLG copolymer is a PLGH copolymer.

11. The method of claim 7 wherein the organic solvent is water-soluble.

12. The method of claim 7 wherein the organic solvent is N-methylpyrrolidone, dimethylacetamide, dimethylformamide, dimethylsulfoxide, or a polyethyleneglycol.

13. The method of claim 7 wherein the bioactive agent comprises a peptide, a protein, a steroid, a prostaglandin, a hormone or hormone regulating substance, an anti-psychotic, an anti-inflammatory, an analgesic or a nucleic acid.

14. The method of claim 7 wherein the bioactive agent is risperidone, octreotide, leuprolide, or GHRP-1.

15. The method of claim 7 wherein the constant release copolymer composition comprises about 4-6 wt % of the PLG oligomer.

16. The method of claim 7 wherein the PLG oligomer comprises at least about 50 mole % lactide residues and has a weight average molecular weight of about 5-10 kDa.

17. The method of claim 7 wherein the PLG oligomer has at least about a 65 mole % of lactide residues.

18. The method of claim 7 wherein the oligomer comprises 100 mole % of lactide residues.

19. The method of claim 7 wherein the PLG oligomer has a weight average molecular weight of about 7-8 kDa.

20. A method of administering a bioactive agent to a patient in need thereof, over a prolonged period of time, wherein a substantially constant rate of release of the bioactive agent is achieved, comprising administering to the patient in need thereof, the controlled release formulation of claim 1.

21. The method of claim 20 wherein the formulation is administered as a depot.

22. The method of claim 21 wherein the depot is emplaced subcutaneously.

23. The method of claim 20 wherein the patient suffers from a malcondition, the bioactive agent being adapted to treat, arrest, or palliate the malcondition.

24. The method of claim 23 wherein the malcondition is prostate cancer and the agent comprises leuprolide.

25. The method of claim 23 wherein the malcondition is acromegaly and the agent comprises octreotide.

26. The method of claim 23 wherein the malcondition is psychosis and the agent comprises risperidone.

27. The method of claim 23 wherein the malcondition is pain and the agent is an analgesic or an anti-inflammatory.

28. A kit adapted for administration to a patient of the controlled release formulation of claim 1 comprising a first container comprising the bioactive agent, and a second container comprising the constant release copolymer composition, optionally dissolved in the organic solvent, or, optionally, a third container comprising the organic solvent, wherein the kit is adapted such that respective contents of the first, the second, and optionally the third container can be mixed for administration to the patient, optionally further comprising instructional material.

29. The kit of claim 28 wherein the first container, the second container, or both, comprise a syringe.

30. The kit of claim 29 wherein the first container comprises a first syringe and the second container comprises a second syringe, and the kit further comprises a coupling such that the contents of the first syringe and the second syringe can be mixed by reciprocally interchanging the contents of the first syringe and the second syringe.

31. The kit of claim 28 wherein the bioactive agent is present in the first container in form of a dry, dehydrated, or lyophilized solid prior to mixing with the contents of the second and, optionally, the third container.

32. The kit of claim 28 wherein the respective contents of the containers have previously been sterilized.

33. The kit of claim 32 wherein the respective contents of the containers have previously been sterilized by gamma radiation or by electron beam radiation.

* * * * *

UNITED STATES PATENT AND TRADEMARK OFFICE
CERTIFICATE OF CORRECTION

| | | |
|---|---|---|
| PATENT NO. | : 8,877,225 B2 | Page 1 of 1 |
| APPLICATION NO. | : 12/477805 | |
| DATED | : November 4, 2014 | |
| INVENTOR(S) | : Norton et al. | |

It is certified that error appears in the above-identified patent and that said Letters Patent is hereby corrected as shown below:

In the claims

In column 22, line 35, in Claim 28, delete "bio active" and insert --bioactive--, therefor Signed and Sealed this
Third Day of November, 2015

Michelle K. Lee
*Director of the United States Patent and Trademark Office*